United States Patent [19]
Takano et al.

[11] Patent Number: 5,726,188
[45] Date of Patent: Mar. 10, 1998

[54] OPTICALLY ACTIVE IMIDAZOLIDINONE DERIVATIVES AND PROCESSES FOR PREPARING THEM

[75] Inventors: Yasuo Takano, Kazo; Kei Okazaki, Nogi-machi; Takashi Hirayama, Washimiya-machi; Tsuyoshi Anraku, Nogi-machi, all of Japan

[73] Assignee: Kyorin Pharmaceutical Co., Ltd., Tokyo, Japan

[21] Appl. No.: 612,827

[22] PCT Filed: Sep. 12, 1994

[86] PCT No.: PCT/JP94/01505

§ 371 Date: Mar. 15, 1996

§ 102(e) Date: Mar. 15, 1996

[87] PCT Pub. No.: WO95/07905

PCT Pub. Date: Mar. 23, 1995

[30] Foreign Application Priority Data

Sep. 17, 1993 [JP] Japan ................................. 5-254983
Sep. 9, 1995 [JP] Japan ................................. 60242264

[51] Int. Cl.⁶ .................... A61K 31/445; C07D 401/04
[52] U.S. Cl. .................................... 514/326; 546/210
[58] Field of Search .......................... 546/210; 514/326

[56] References Cited

U.S. PATENT DOCUMENTS

| | | | |
|---|---|---|---|
| 3,196,152 | 7/1965 | Wright et al. | 548/316.4 |
| 3,355,457 | 11/1967 | Wright et al. | 548/316.4 |
| 3,459,757 | 8/1969 | Wright, Jr. | 514/401 |
| 4,011,238 | 3/1977 | Fontanella et al. | 514/401 |
| 5,300,515 | 4/1994 | Takano et al. | |
| 5,401,750 | 3/1995 | Varasi et al. | 514/299 |

FOREIGN PATENT DOCUMENTS

95/07904  3/1995  WIPO .

*Primary Examiner*—Ceila Chang
*Attorney, Agent, or Firm*—Oblon, Spivak, McClelland, Maier & Neustadt, P.C.

[57] ABSTRACT

An optically active imidazolidinone derivative represented by general formula (1), having a cholinergic activity (a muscarine $M_1$ activity) and being useful for treating senile dementia, a pharmacologically acceptable acid-addition salt thereof, and a process for producing the same, wherein R and $R^1$ may be the same or different and each represents hydrogen, halogen, optionally halogenated lower alkyl, lower alkoxy, lower alkylthio, lower alkoxycarbonyl, nitro, amino or cyano; and n represents 1 to 4.

11 Claims, No Drawings

OPTICALLY ACTIVE IMIDAZOLIDINONE DERIVATIVES AND PROCESSES FOR PREPARING THEM

SPECIFICATION

This application is a 371 of PCT/JP94/01505 filed Sep. 12, 1994.

1. Technical Field

The present invention relates to optically active imidazolidinone derivatives with cholinergic activity (muscarine $M_1$ activity) or pharmaceutically acceptable acid addition salts, processes for preparing them and therapeutic drugs for senile dementia having them as effective components.

2. Background Techniques

In recent years, as the average span of life becomes long, the senile dementia such as Alzheimer type senile dementia has posed a significant problem both medically and socially.

The patients of dementia show symptom such as loss of intellectual ability, disturbance of memory, disturbance of abstract thinking, verbal aphasia, apraxia, disorientation, etc. and the disorder of basic functions lies in the disturbance of the formation of memory or the expressive ability of retained memory. Until today, however, there have been almost no medicaments that can treat this effectively, hence immediate development of therapeutic drugs is desired.

It is said that the disturbances of learning and memory in the patients of dementia (in particular, senile dementia and Arzheimer type senile dementia) are particularly associated with the decrease in central cholinergic function. Hence, such compounds that have this central cholinergic function, that is, the functional activity of acetylcholine being a nerve transmitter can be used for the treatment of patients of dementia (Science, 217, 408 (1982): R. I. Bartus et al.).

It is said that, among the degenerative diseases of nerve due to decreased central cholinergic function, the core symptoms relating particularly to the disturbances of memory, recognition, etc. are due to the decreased function of central cholinergic nerve and conventionally, for improving these core symptoms, administration of acetylcholinesterase inhibitor such as physostigmine, administration of acetylcholine precursors such as choline and lecithin, administration of drugs acting on the cholinergic receptor such as arecoline, and the like have been attempted (e.g. Dementia, 1, 188 (1987) etc.). All of these attempts however have many problematic points that they are ineffective in the therapy, that, even if slight effect may be developed, adverse effect is strong or the therapeutic range is narrow, and the like.

Moreover, the optically active imidazolidinone derivatives of the invention are not described in the literatures, but, for compounds relat.ing to racemic form, there is U.S. Pat. No. 3,459,757 (Aug. 5, 1969) showing a following general formula.

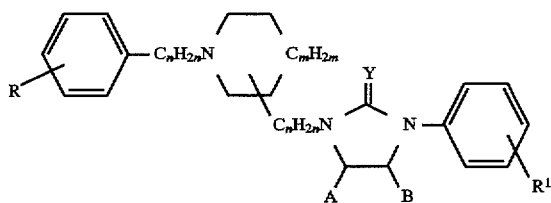

(wherein R and $R^1$ denote hydrogen atoms, halogen atoms, lower alkyl groups, lower alkoxy groups or trifluoromethyl groups, A and B denote hydrogen atoms or lower alkyl groups, Y denotes an oxygen atom or sulfur atom, m denotes 0 to 1, and n denotes 0 to 2).

In this patent, however, a description that the compounds are effective for the CNS depressant properties, muscle relaxant, etc. at a level of nontoxicity can be found, but there is no description at all that they have muscarine ($M_1$) activity.

In addition, a compound represented by a following formula

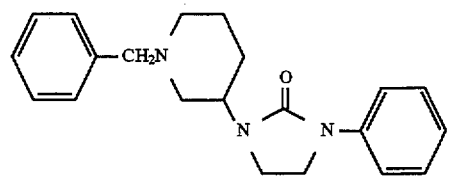

is described in the example, but this compound is of racemic form and there is no sign at all that it was developed as a medicinal drug.

The purpose of the invention is to provide the therapeutic drugs for senile dementia which activate the central cholinergic function of the patients of dementia (in particular, senile dementia and Arzheimer type senile dementia) and which are effective for the therapy of the disturbance of memory and having high safety, taking the present status of the patients of dementia aforementioned into consideration.

DISCLOSURE OF THE INVENTION

As a result of diligent studies searching for the therapeutics articularly for the disturbance of memory among various symptoms of dementia for the purpose of developing novel therapeutics for senile dementia, the inventors have found that the inventive optically active imidazolidinone derivatives and their acid adducts have excellent cholinergic activity (muscarine $M_1$ activity).

Namely, according to the invention, it has been found that the imidazolidinone derivatives represented by a general formula (1)

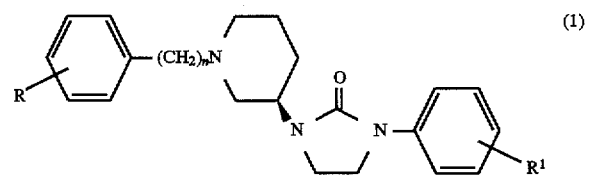

(wherein R and $R^1$ denote identically or differently hydrogen atoms, halogen atoms, lower alkyl groups which may be substituted by halogen atom, lower alkoxy groups, lower alkylthio groups, lower alkoxycarbonyl groups, nitro groups, amino groups or cyano groups, and n denotes 1 to 4), or their acid adducts have surprisingly excellent cholinergic activity (muscarine $M_1$ activity), leading to the completion of the invention.

Comparing the effect of drugs of the inventive compounds (R form) with that of corresponding racemic form and antipode (S form), as described later, it was found that, in the in vitro muscarine ($M_1$) activity, R form had about 120 times as excellent as activity over S form and about 3 times over racemic form and additionally that the in vivo improving action on the disturbance of learning could be recognized only for R form with significant difference.

Moreover, from clinical impressions, common symptoms i.e. convulsive actions were seen in the administration groups of racemic form and S form, and further, with regard to the toxicity, even at a dose that all cases (4/4) brought about death in the administration group of racemic form, that is, even at 1200 mg/kg p.o., problems did not arise at any rate in the administration group of R form. Based on this fact, it was made clear that undesirable actions with racemic form (convulsive common symptoms and toxicity) depended on the S form.

The optically active imidazolidinone derivatives (R form) in the invention, therefore, are therapeutic drugs for senile dementia which activate the central cholinergic function of the patients of dementia (in particular, senile dementia and Arzheimer type senile dementia) and which are effective for the therapy of the disturbance of memory and having high safety.

In the description of the general formula (1) of the invention, for "lower alkyl", straight chain or branched ones with carbon atoms of 1 to 6 such as methyl, ethyl, n-propyl and isopropyl are mentioned.

For "halogen atom", fluorine, chlorine, bromine and iodine are mentioned, for "lower alkoxy", straight chain or branched ones with carbon atoms of 1 to 4 such as methoxy, ethoxy and propoxy are mentioned, for "lower alkoxycarbonyl group", methoxycarbonyl, ethoxycarbonyl, etc. are mentioned, and "amino group" may be substituted by acyls, for example, acetyl etc. or may be substituted by one or two lower alkyl groups. For "protective group of amino group", for example, lower acyl groups such as acetyl and propionyl, lower alkoxycarbonyl groups such as ethoxycarbonyl and tert-butoxycarbonyl, and benzyl group are mentioned.

For "eliminating group", for example, halogen atoms such as fluorine, chlorine, bromine and iodine, and sulfonyloxy groups such as p-toluenesulfonyloxy group and methanesulfonyloxy group are mentioned.

"Acid addition salts" are pharmaceutically acceptable salts with, for example, hydrochloric acid, citric acid, succinic acid, fumaric acid, maleic acid, etc.

The inventive compounds represented by the general formula (1) can be prepared through, for example, four kinds of preparative processes shown below ([A] through [D]).

[A] The compounds represented by the general formula (1) can be synthesized by submitting compounds represented by a general formula (2)

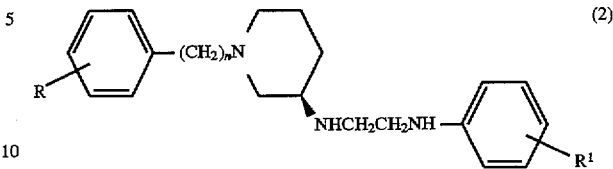

(R,R¹ and n are as described above), to carbonyl-insertion reaction, for example, by reacting for 1 to 5 hours at 0° to 150° C. in a suitable solvent such as tetrahydrofuran, dioxane, benzene, acetonitrile or chloroform or without solvent, using a cyclizing agent such as N,N'-carbonyldiimidazole, phosgene or diethyl carbonate.

The compounds represented by the general formula (2) can be synthesized according to following scheme.

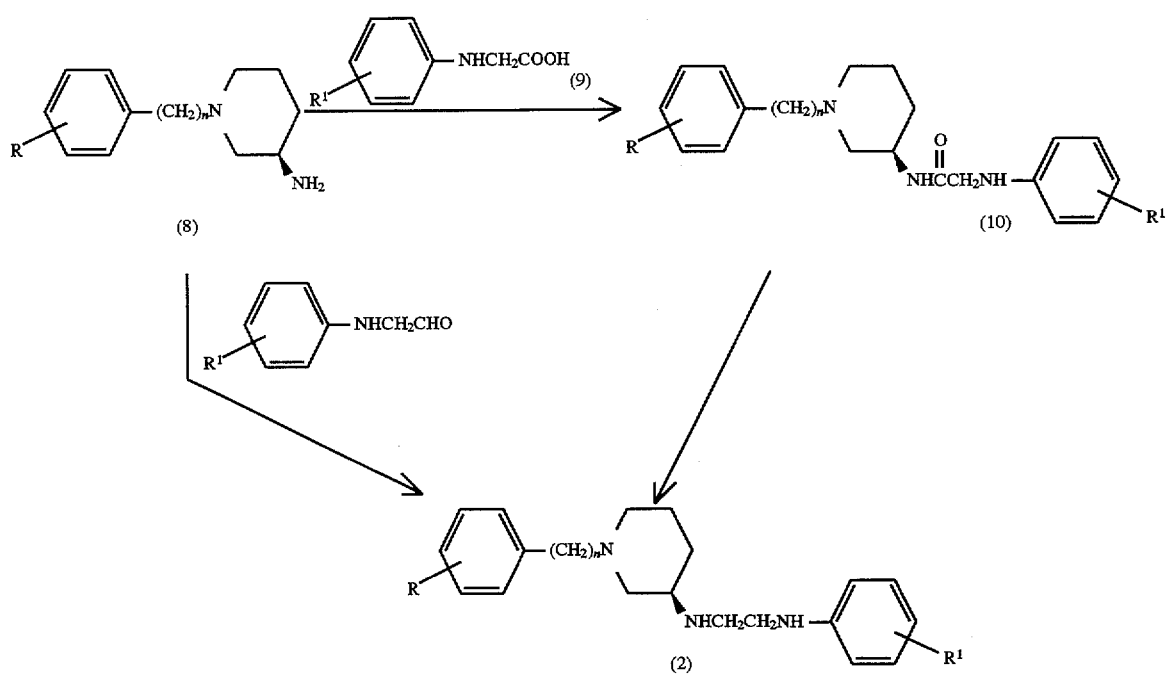

(R,R¹ and n are as described above).

Namely, they can be synthesized in a way that optically active 3-amino-1-aralkyl piperidine (8) is reacted with a suitable N-phenylglycine (9) for 1 to 7 hours at 0° to 25° C. in a suitable solvent such as tetrahydrofuran, N,N-dimethylformamide, benzene, acetonitrile, dichloromethane or chloroform in the presence of a suitable base such as triethylamine, pyridine or N,N-dimethylaminopyridine, using a condensing agent such as N,N'-dicyclohexylcarbodiimide (DCC), diethyl phosphoryl cyanide (DEPC), 1-(3-dimethylaminopropyl)-3-ethylcarbodiimide hydrochloride (EDCI) or chloroformic ester (acid anhydride process) to give amide form (10), and this is reacted for 1 to 10 hours at 20° C. to boiling point of solvent in a suitable solvent such as ether, tetrahydrofuran, dioxane or benzene in the presence of a reducing agent such as lithium aluminumhydride or borane complex (e.g. borane-tetrahydrofuran complex etc.).

Moreover, they can also be synthesized by reacting optically active 3-amino-1-aralkylpiperidine (8) with corresponding aldehyde form (11) for 2 to 6 hours at 20° C. to boiling point of solvent in a suitable solvent such as toluene or xylene in the presence of a reducing agent such as sodium borohydride or sodium cyanoborohydride.

The compounds represented by the general formulae (9) and (11) referred to so here are publicly known and can be synthesized according to, for example, Japan Patent Kokai No. Sho 57-116003, J. Med. Chem., 8, 405 (1965), J. Chem. Soc., 307 (1949), J. Org.. Chem., 23, 186 (1958), German Patent No. DE 3,300,004, etc.

[B] The compounds represented by the general formula (1) can also be synthesized by reacting compounds represented by a general formula (3)

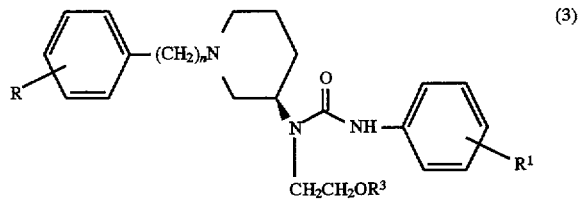

(wherein R,R$^1$ and n are as described above, and R$^3$ denotes a hydrogen atom, lower alkyl group or aralkyl group), for 2 to 10 hours at 90° to 150° C. in an acid such as hydrobromic acid or hydrochloric acid or a halogenating agent such as thionyl chloride or phosphorus tribromide.

The compounds represented by the general formula (3) can be synthesized according to following scheme.

Namely, they can be synthesized in a way that optically active 3-amino-1-aralkylpiperidine (8) is reacted with corresponding carboxylic acid form or its acid halide (12) for 2 to 5 hours at 0° to 25° C. in a suitable solvent such as tetrahydrofuran, benzene, dichloromethane or chloroform in the presence of a condensing agent such as N,N'-dicyclohexylcarbodiimide (DCC), diethyl phosphoryl cyanide (DEPC) or 1-(3-dimethylamiopropyl)-3-ethylcrbodiimide hydrochloride (EDCI) (acid anhydride process using chloroformic ester may also be possible) or in the presence of a suitable base such as triethylamine or pyridine to give amide form (13), this is reacted for 1 to 10 hours at 0° C. to boiling point of solvent in a suitable solvent such as tetrahydrofuran, ether, dioxane or benzene in the presence of a reducing agent such as lithium aluminum hydride or borane complex (e.g. borane-tetrahydrofuran complex etc.) to convert to amine form (14), and this is reacted with a suitable isocyanic ester (15) in a suitable solvent such as tetrahydrofuran, benzene, dichloromethane, chloroform or N,N-dimethylformamide or without solvent in the presence of a suitable base such as triethylamine or pyridine.

The compounds represented by the general formula (8), that is, optically active 3-amino-1-aralkylpiperidines (8) are novel compounds and can be synthesized according to following scheme.

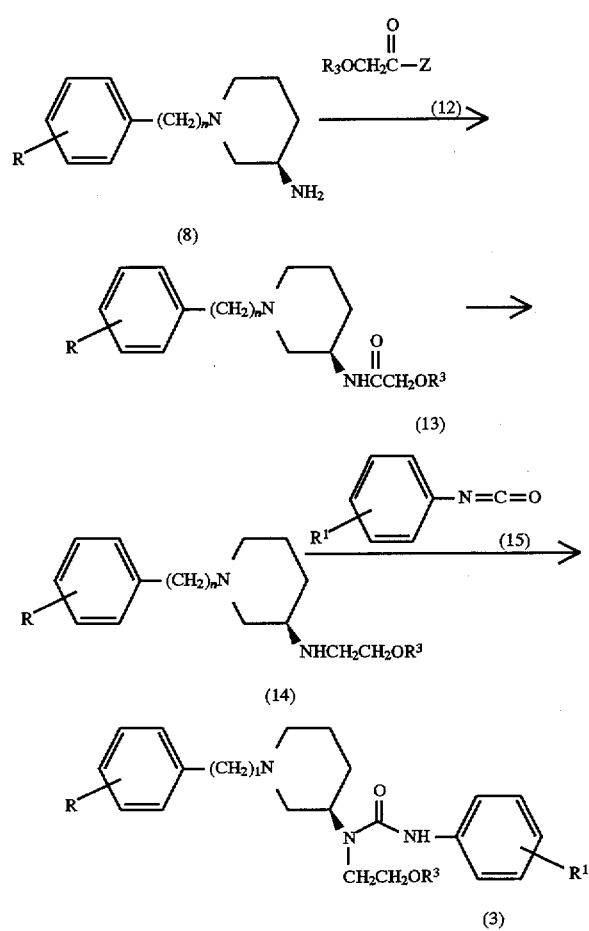

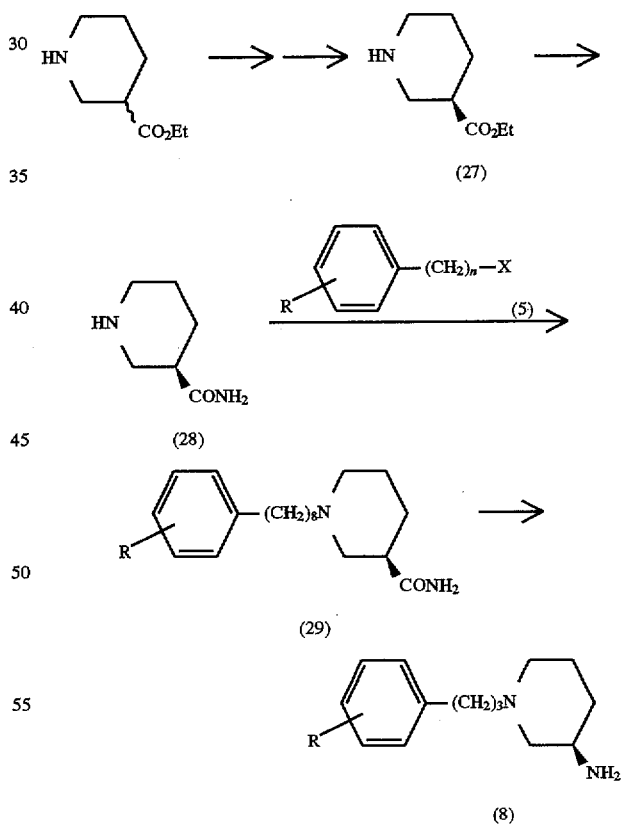

(R and n are as described above, and X denotes an eliminating group).

Namely, (R)-ethyl nipecotate (27) obtained through optical resolution by a published method, a method described in Recueil. Tray. chim. Pays-Bas. 70, 899 (1951), Chem. Ber., 102, 2864 (1969), is reacted with aqueous ammonia for 2 to (Z denotes a hydroxyl group or halogen atom, and R,R$^1$,R$^3$ and n are as described above).

4 days at 0° to 30° C. to give nipecotamido (28), and this can be converted to amide form (29) by reacting with aralkyl form (5) for 2 to 10 hours at 0° to 20° C. in a suitable solvent such as tetrahydrofuran, acetonitrile, dichloromethane or ethanol or in a mixture thereof in the presence of a suitable base such as triethylamine, pyridine or N,N-dimethylaminopyridine.

By conducting retention of configuration reaction such as Hofmann rearrangement reaction on the amide form (29) obtained here, optically active 3-amino-1-aralkylpiperidine (8) can be synthesized.

[C] The compounds represented by the general formula (1) can also be synthesized by reacting compounds represented by a general formula (4)

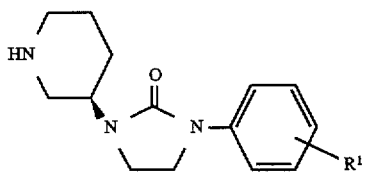

(wherein $R^1$ is as describe above), with compounds represented by a general formula (5)

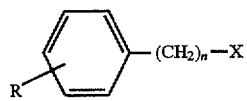

(wherein R, X and n are as described above), for 2 to 10 hours at 25° to 100° C. in a suitable solvent such as tetrahydrofuran, acetonitrile, dichloromethane or ethanol or mixture thereof in the presence of a suitable base such as potassium carbonate, triethylamine, pyridine or N,N-dimethylaminopyridine.

The compounds represented by the general formula (4) can be synthesized by deprotecting compounds represented by a general formula (19)

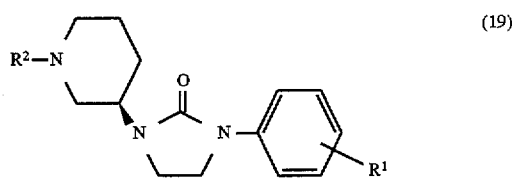

(wherein $R^1$ is as-described above, and $R^2$ denotes a protective group of amino group), for example, by reacting for 1 to 7 hours at 20° to 120° C. in a suitable solvent such as tetrahydrofuran or ethanol or without solvent in the presence of an acid such as hydrochloric acid or hydrobromic acid.

Moreover, in the case of $R^2$ being a benzyl group, they can be synthesized through catalytic hydrogenation. Namely, they can be synthesized by reacting for 1 to 5 hours at 20° to 100° C. under an applied hydrogen pressure of 50 to 70 kg/cm$^3$ in a suitable solvent such as methanol, ethanol or acetic acid in the presence of a catalyst such as palladium carbon (Pd-C), platinum carbon (Pt-C), rhodium carbon (Rh-C), platinum oxide (PtO$_2$) or rhodium alumina (Rh-Al$_2$O$_3$), or by reacting together with stoichiometric ammonium formate for 2 to 10 hours at 20° C. to boiling point of solvent in a suitable solvent such as methanol, ethanol or water or a mixed solvent thereof in the presence of a catalyst such as palladium carbon (Pd-C), platinum carbon (Pt-C), rhodium carbon (Rh-C), platinum oxide (PtO$_2$) or rhodium alumina (Rh-Al$_2$O$_3$).

The compounds represented by the general formula (19) can be synthesized according to following scheme (I, II or III).

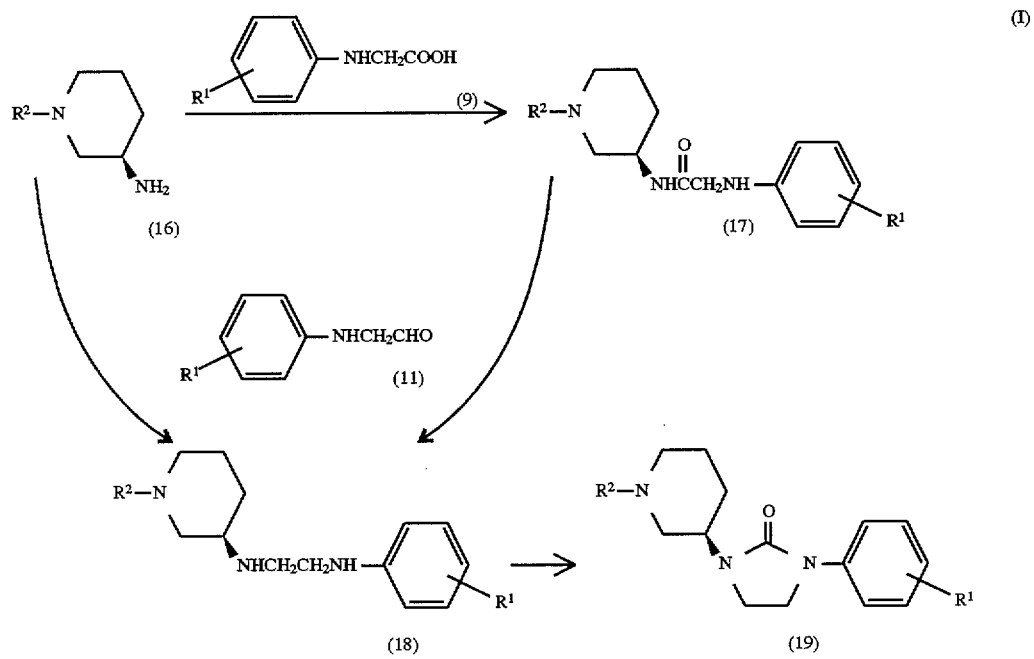

($R^1$ and $R^2$ are as described above.)

Namely, they can be synthesized in a way that optically active 3-aminopiperidine (16) with amino group protected is reacted with a suitable N-phenylglycine (9) for 1 to 7 hours at 0° to 25° C. in a suitable solvent such as tetrahydrofuran, N,N-dimethylformamide, benzene, acetonitrile, dichloromethane or chloroform in the presence of a suitable base such as triethylamine, pyridine or N,N-dimethylaminopyridine, using a suitable condensing agent such as N,N'-dicyclohexylcarbodiimide (DCC), diethyl phosphoryl cyanide (DEPC), 1-(3-dimethylaminopropyl)-3-ethylcrbodiimide hydrohloride (EDCI) or chloroformic ester (acid anhydride process) to give amide form (17), this is reacted for 1 to 10 hours at 20° C. to boiling point of solvent in a suitable solvent such as ether, tetrahydrofuran, dioxane or benzene in the presence of a reducing agent such as lithium aluminum hydride or borane complex (e.g. borane-tetrahydrofuran complex etc.), to convert to ethylenediamine form (18), and this is submitted to carbonyl-insertion reaction, for example, by reacting for 1 to 5 hours at 0° to 150° C. in a suitable solvent such as tetrahydrofuran, dioxane, benzene, acetonitrile or chloroform or without solvent, using a cyclizing agent such as N,N'-cabonyldiimidazole, phosgene or diethyl carbonate.

Moreover, the ethylenediamine form (18) can also be synthesized by reacting optically active 3-aminopiperidine (16) with amino group protected with corresponding aldehyde form (11) for 2 to 6 hours at 20° C. to boiling point of solvent in a suitable solvent such as toluene or xylene in the presence of a reducing agent such as sodium borohydride or sodium cyanoborohydride.

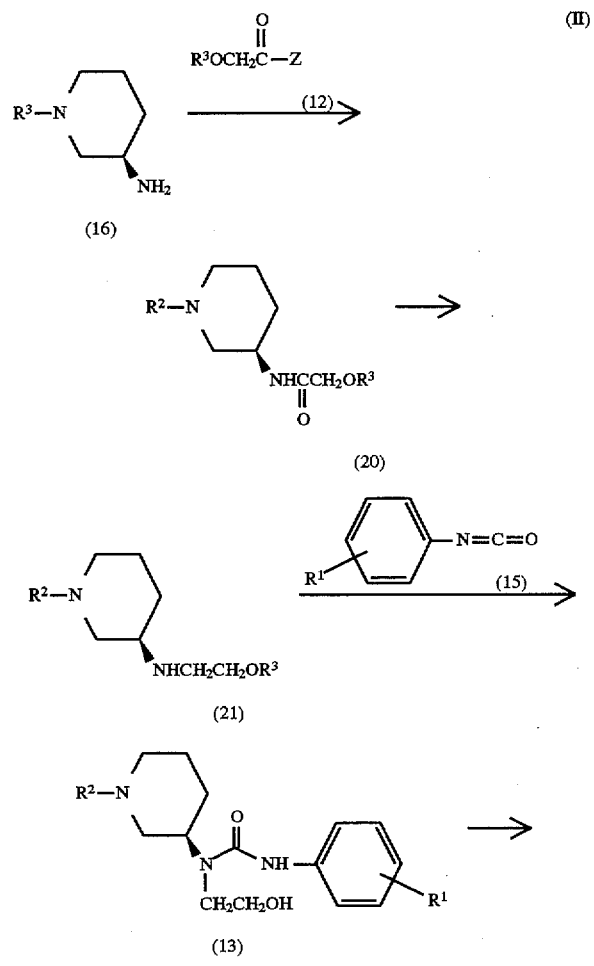

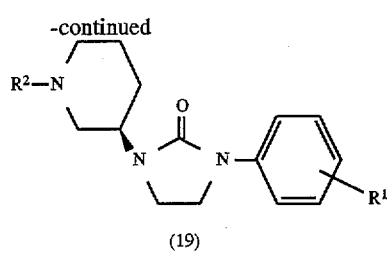

(Z denotes a hydroxyl group or halogen atom, and $R^1, R^2, R^3$ and n are as described above).

Namely, they can be synthesized in a way that optically active 3-aminopiperidine (16) with amino group protected is reacted with corresponding carboxylic acid form or its acid halide (12) for 2 to 5 hours at 0° to 25° C. in a suitable solvent such as tetrahydrofuran, benzene, dichloromethane or chloroform in the presence of condensing agent such as N,N'-dicyclohexylcarbodiimide (DCC), diethyl phosphoryl cyanide (DEPC) or 1-(3-dimethylaminopropyl)-3-ethylcarbodiimide.hydrochloride (EDCI) (acid anhydride process using chloroformic ester may also be possible) or in the presence of a suitable base such as triethylamine or pyridine to give amide form (20), this is reacted for 1 to 10 hours at 0° C. to boiling point of solvent in a suitable solvent such as tetrahydrofuran, ether, dioxane or benzene in the presence of a reducing agent such as lithium aluminum hydride or borane complex (e.g. borane-tetrahydrofuran complex etc.) to convert to amine form (21), this is reacted with a suitable isocyanic ester (15) in a suitable solvent such as tetrahydrofuran, benzene, dichloromethane, chloroform or N,N-dimethylformamide or without solvent in the presence of a suitable base such as triethylamine or pyridine to give urea form (22), then $R^3$ is selectively deprotected to give alcohol form (23), and this is reacted for 2 to 5 hours at 90° to 150° C. in a halogenating agent such as thionyl chloride or phosphorus tribromide.

The compounds represented by the general formula (4) can also be synthesized through one process without passing through the general formula (19) by reacting urea form (22) obtained as above for 2 to 5 hour at 90° to 150° C. in an acid such as hydrobromic acid or hydrochloric acid.

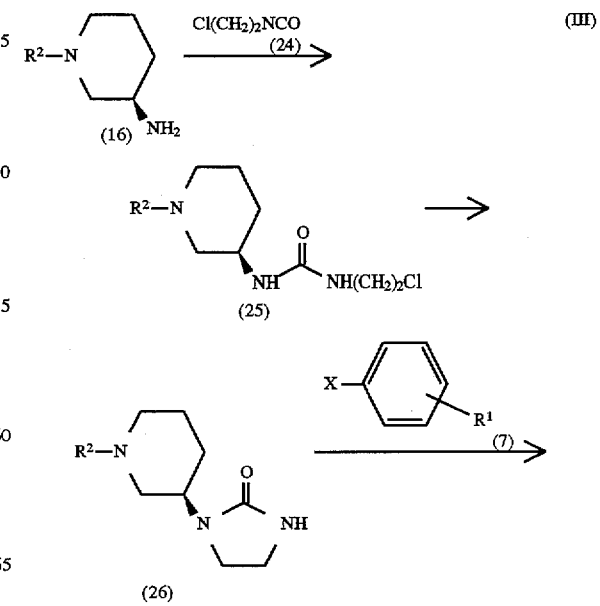

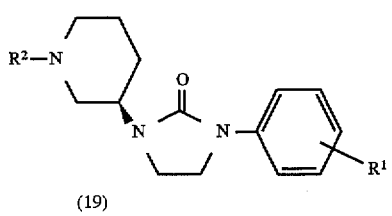

(19)

(wherein $R^1$ and $R^2$ are as described above, and X denotes an eliminating group).

Namely, they can also be synthesized in a way that optically active 3-aminopiperidine (16) with amino group protected is reacted with chloroethyl isocyanate (24) for 1 to 10 hours at 25° to 80° C. in a suitable solvent such as tetrahydrofuran, acetonitrile, N,N-dimethylformamide or methylene chloride to give urea form (25), this is intramolecular cyclized in the presence of a suitable base such as sodium hydride to give compound (26), and this is reacted with compounds of a general formula (7) in a suitable solvent such as tetrahydrofuran, acetonitrile or N,N-dimethylformamide, using a suitable base such as sodium hydride or N,N-dimethylaminopyridine.

Moreover, the compounds represented by the general formula (16), that is, optically active 3-aminopiperidines with amino group protected are also novel compounds and can be synthesized according to following scheme.

compound (33), hydrolyzing this to convert to carboxylic acid form (34) or its acid chloride form (35), and conducting Curtius transition reaction.

[D] The compounds represented by the general formula (1) can also be synthesized by reacting compounds represented by a general frmula (6)

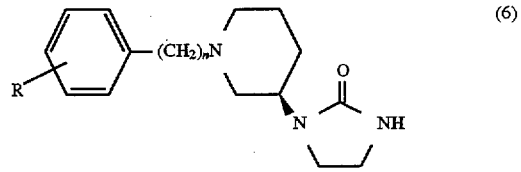

(6)

(wherein R and n are as described above), with compounds represented by a general formula (7)

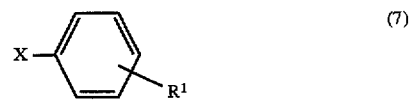

(7)

(wherein $R^1$ is as described above, and X denotes an eliminating group), for 1 to 10 hours at 25° to 80° C. in a suitable solvent such as tetrahydrofuran, acetonitrile or N,N-dimethylformamide, using a suitable base such as sodium hydride.

The compounds represented by the general formula (6) can be synthesized according to following scheme.

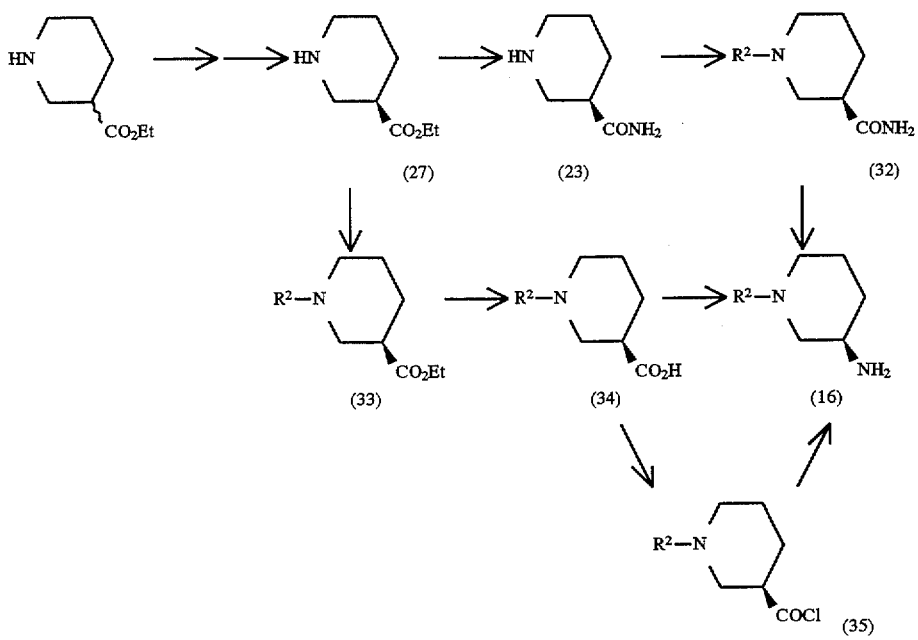

($R^2$ is as described above).

Namely, in the synthesis of said optically active 3-amino-1-aralkylpiperidine (8), they can be synthesized by converting to amide form (32) introduced with a protective group of amino group, for example, protective group ($R^2$) using ethyl chloroformate in place of reacting aralkyl form (5) with nipecotic amide (28), and by similar process using Hofmann rearrangement reaction. Further, optically active 3-aminopiperidine (16) with amino group protected can also be synthesized by introducing a protective group to amino group of optically active ethyl nipecotate (27) to give

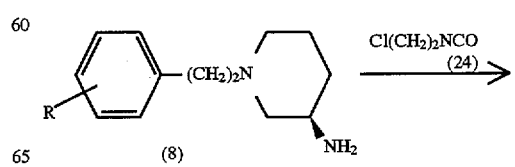

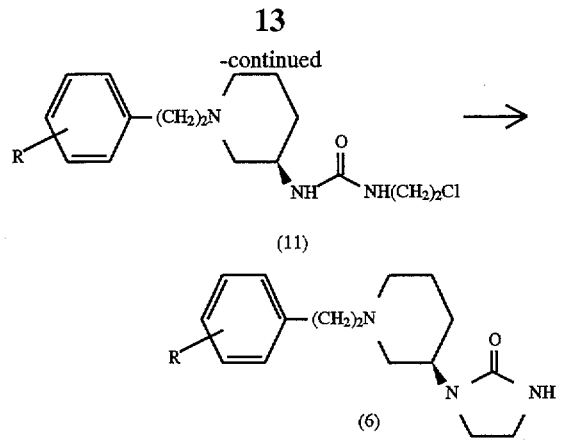

(wherein R and n are as described above).

Namely, they can be synthesized in a way that optically active 3-amino-1-aralkylpiperidine (8) is reacted with chloroethyl isocyanate (24) for 1 to 10 hours at 25° to 80° C. in a suitable solvent such as tetrahydrofuran, acetonitrile, N,N-dimethylformamide or methylene chloride to give urea form (30), and this is intramolecular cyclized in the presence of a suitable base such as sodium hydride.

Moreover, the compounds represented by the general formula (1) and general formula (4) and the compounds represented by the general formula (8) and general formula (16) can also be converted to optically active compounds (1), (4), (8) and (16) by submitting their racemic form themselves to optical resolution with optical resolving agent, for example, dibenzoyltartaric acid or the like.

When pharmaceutically acceptable acid addition salts of the compounds represented by the general formula (1) are required, they can be obtained by reacting synthesized imidazolidinone derivatives with, for example, inorganic acids such as hydrochloric acid or organic acids such as maleic acid.

Best embodiment for putting the invention into practice

The preparative examples and the examples of the invention will be described to illustrate the invention in more detail.

(EXAMPLE 1)

(R)-1-(4-florophenyl)-3-[3-(1-phenylmethyl) piperidyl]-2-imidazolidinone

To a 30 ml distilled tetrahydrofuran solution of 9.70 g (29.6 mmol) of (R)-N-4-florophenyl-N'-3-(1-phenylmethyl) -piperidylethylenediamine in a 200 ml round-bottomed flask were added 9.61 g (2 eg.) of N,N'-carbonyldiimidazole (CDI) at room temperature, and the mixture was refluxed for 1 hour under heat. Thereafter, solvent was distilled off at 100° C. in an oil bath under atmospheric pressure to obtain the residue, which was heated for 1 hour at about 110° C. and allowed to stand for 2 days. To this residue were added 200 ml of methylene chloride to dissolve, and further 200 ml of water were added to extract and separate the organic layer. The aqueous layer was made to be pH of 12 or higher with 2N sodium hydroxide, which was extracted with methylene chloride (100 ml×2) These methplene chloride layers were combined with previously extracted layer, dried over anhydrous sodium sulfate, and then solvent was distilled off under reduced pressure to obtain a brown oil. This was purified by column chromatography (silica gel, n-hexane:ethyl acetate=3:5) and then recrystallized to obtain 3.56 g (yield 34 %) of title compound.

m.p. 122°–123° C. (2-propanol) colorless prisms $[\alpha]_D^{25}$= +11° (1=50 c. 5.0 chloroform) Elemental analysis (%); As $C_{21}H_{24}FN_3O$ Calculated; C: 71.36 H: 6.84 N: 11.89 Found; C: 71.56 H: 6.89 N: 11.81

The starting material, (R)-N-4-fluorophenyl-N'-3-(1-phenylmethyl)piperidylethylenediamine was synthesized as follows:

(Referential Example 1)

(R)-2-(N-4-fluorophenyl)amino-N'-3-(1-phenylmethyl) piperidylacetamide

To a 100 ml dried N,N'-dimethylformamide solution of 8.18 g (43.0 mmol) of (R)-1-phenylmethyl-3-aminopiperidine in a 200 ml round-bottomed flask were added 7.27 g (1 eg.) of N-4-fluorophenylglycine at room temperature. This was cooled to 10° C. and 6.87ml (1 eg.) of diethyl phosphoryl cyanide (DEPC, 95 %) and 6 ml (1 eg.) of triethylamine were added dropwise in turn. After dropwise addition, the reaction mixture was stirred for 2 hours at room temperature. After allowed to stand overnight, the reaction mixture was distilled off under reduced pressure and 150 ml of water were added to the residue, which was stirred for 15 minutes, then deposited oily product was separated. The separated oily product was dissolved into 100 ml of methylene chloride and, after washed with saturated aqueous solution of sodium hydrogen carbonate and saturated aqueous solution of sodium chloride in turn, the organic layer was separated. The aqueous layer was extracted again with methylene chloride (100 ml×3). In addition, to the filtrate at the time of having separated the oily product were added 250 ml of water. This was extracted with ethyl acetate (100 ml×2) and washed with saturated aqueous solution of sodium chloride, then the organic layer was separated. Previous methylene chloride, then the organic layer was separated. Previous methylene chloride layer was combined with ethyl acetate layer and, after dried over anhydrous sodium sulfate, solvent was distilled off under reduced pressure to obtain brown residue. This was purified by column chromatography (silica gel, ethyl acetate) to obtain 13.3 g (yield 91%) of title compound as a brown oil.

$[\alpha]_D^{25}$=−15° (1=50, c. 5.0, chlorform) MASS; As $C_{20}H_{24}FN_3$ O m/e; 341 (M⁺), 217, 173, 124, 91 (base)

(Referential Example 2)

(R)-N-4-fluorophenyl-N'-3-(1-phenylmethyl) piperidyl ethylenediamine

To a 100 ml dioxane suspension of 5.14 g (3.5 eg.) of lithium aluminum hydride in a 500 ml round-bottomed flask was added dropwise a 180 ml dioxane solution of 13.2 g (38.7 mmol) of (R)-2-(N-4-fluorophenyl)amino-N'-3-(1-phenylmethyl)-piperidylacetomide by portions at room temperature. After dropwise addition, the reaction mixture was returned to room temperature and it was stirred for 1 hour and further refluxed for 6 hours. After allowed to stand overnight, the reaction mixture was added carefully into about 200 ml of ice water and it was stirred for 30 minutes. Concentrated hydrochloric acid was added to this to make pH 1 or higher, which was extracted with ethyl acetate (200 ml). The aqueous layer was separated and the organic layer was extracted with 2N hydrochloric acid (200 ml×3). Combining these with previous aqueous layer, pH was made to be 12 or higher using potassium hydroxide under cooling with ice. After added with ethyl acetate (300 ml) to this, the mixture was stirred for 30 minutes and further celite was added to filter off. The filtrated residue was washed well with ethyl acetate and the organic layer of liltrate was separated. The aqueous layer was extracted with ethyl acetate (30 ml×3), which were combined with previous organic layer. After dried over anhydrous sodium sulfate, solvent was distilled off under reduced pressure to obtain brown residue. This was purified by column chromatography (alumina, n-hexane:ethyl acetate=2:5) to obtain 9.70 g (yield 77 %) of title compound as a brown oil.

$[\alpha]_D^{25}$=−9.2° (l=50, c. 8.7, ethyl acetate) 1H-NMR (TMS in CDCl$_3$, 90MHz) δ. 1.15–2.28 (6H, m), 2.42–2.94 (5H, m), 2.97–3.23 (2H, m), 3.49 (2H, s), 6.45–6.61 (2H, m), 6.77–6.97 (2H, m), 7.28 (5H, s)

(EXAMPLE 2)

(R)-1-(4-chlorophenyl)-3-[3-(1-phenylmethyl) piperidyl]-2-imidazolidinone

By the similar method to Example 1, title compound was synthesized.

m.p. 158°–160° C. (ethyl acetate: n-hexane) colorless prisms $[\alpha]_D^{26}$=+15° (l=50, c. 3.0, chloroform) Elemental analysis (%); As C$_{21}$H$_{24}$ClN$_3$O Calculated; C: 68.19 H: 6.54 N: 11.36 Found; C: 68.23 H: 6.64 N: 11.41

The starting material, (R)-N-4-chlorophenyl-N'-3-(1-phenylmethyl)piperidylethylenediamine was synthesized as follows:

(Referential Example 3)

(R)-2-(N-4-chlorophenyl)amino-N'-3-(1-phenylmethyl)-piperidylacetamide

By the similar method to Referential example 1, title compound was synthesized.

$[\alpha]_D^{28}$=−19° (l=50, c. 4 9, chloroform) MASS; As C$_{20}$H$_{24}$ClN$_3$ O m/e; 357 (M$^+$), 217, 173, 91 (base)

(Referential Example 4)

(R)-N-4-chlorophenyl-N'-3-(1-phenylmethyl) piperidyl-ethylenediamine

By the similar method to Referential example 2, title compound was synthesized.

$[\alpha]_D^{27}$=−8.4° (l=50, c. 8.6, ethyl acetate) $^1$H-NMR (TMS in CDCl$_3$, 90MHz) δ. 1.05–2.27 (7H, m), 2.39–2.87 (5H, m), 2.93–3.21 (2H, m), 3.48 (2H, s), 6.51 (2H, d, J=9.2 Hz), 7.08 (2H, d, J=8.8Hz), 7.27 (5H, s)

Optically active (R)-1-phenylmethyl-3-aminopiperidine was synthesized as follows:

(Referential Example 5)

(R)-ethyl nipecotate

From (±)-ethyl nipecotate, (R)-ethyl nipecotte (L)-tartrate was synthesized as colorless plates according to the method described in Recueil. Tray. chim. Pays-Bas., 70, 899 (1951).

m.p. 154°–155° C. (ethanol) $[\alpha]_D^{25}$=+53° (l=50, c. 2.0, 0.2 % ammonium molybdate)

Further, the tartrate obtained was hydrolyzed by the similar method to synthesize title compound as a slightly yellowish brown oil.

b.p. 110°–120° C./0.5 mmHg $[\alpha]_D^{28}$=−1.1° (l=50, c. 9.9, water) MASS; As C$_8$ H$_{15}$NO$_2$ m/e; 157 (M$^+$), 128, 112, 84 (base)

(Referential Example 6)

(R)-3-(1-phenylmethyl)nipecotamido

To 14.7 g (93.5 mmol) of (R)-ethyl nipecotate in a 300 ml round-bottomed flask were added 200 ml of concentrated aqueous ammonia at room temperature, and the mixture was allowed to stand for 3 days at room temperature. The reaction mixture was distilled off at a water bath temperature of lower than 40° C. to obtain (R)-nipecotamide as a pale yellow oil. To this were added 100 ml of methylene chloride and 50 ml of ethanol at room temperature, and 15.6 ml (1.2 eg.) of triethylamine were added while cooling with ice. To this reaction mixture were gradually added dropwise 11.1 ml (1 eg.) of benzyl bromide under cooling with ice. After dropwise addition, the mixture was stirred for 10 minutes under cooling with ice and further for 4 hours after returned to room temperature, which was allowed to stand overnight. The reaction mixture was distilled off under reduced pressure and the residue obtained was dissolved into 200 ml of methylene chloride, which was washed with 1N sodium hydroxide and saturated aqueous solution of sodium chloride in turn. The aqueous layer was extracted with methylene chloride (50 ml×3) and, after washed with saturated aqueous solution of sodium chloride, these were combined with previous organic layer and dried over anhydrous sodium sulfate. Solvent was distilled off under reduced pressure and the residue thus obtained was recrystallized to obtain 8.61 g (yield 42 %) of title compound.

m.p. 112°–113° C. (acetonitrile) colorless prisms $[\alpha]_D^{26}$= −18° (l=50, c. 10, ethanol) MASS; C$_{13}$H$_{18}$N$_2$ O m/e; 218 (M$^+$), 174, 127, 91 (base)

(Referential Example 7)

(R)-1-phenylmethyl-3-aminopiperidine

A 120 ml aqueous solution of 16.8 g (8.2 eg.) of sodium hydroxide in a 500 ml round-bottomed flask was cooled with ice and to this was added a 120 ml dioxane solution of 11.2 g (51.3 mmol) of (R)-3-(1-phenylmethyl)nipecotamido, followed by dropwise addition of 3.28 ml (1.24 eg.) of bromine. After dropwise addition, the reaction mixture was reacted for 35 minutes at 65° to 70° C. After allowed to stand overnight, the organic layer was separated. The aqueous layer was extracted with ethyl acetate (100 ml×3), which were combined with previous organic layer. After dried over anhydrous sodium sulfate, solvent was distilled off under reduced pressure to obtain pale yellow residue. This was distilled under reduced pressure to obtain 8.18 g (yield 84 %) of title compound.

b.p. 200°–220° C./0.5 mmHg $[\alpha]_D^{22}$=−13° (l=50, c. 10, ethanol) $^1$H-NMR (TMS in CDCl$_3$, 90MHz) δ. 0.84–1.26 (1H, m), 1.26 (2H, s), 1.42–2.18 (5H, m), 2.42–3.00 (3H, m), 3.48 (2H, s), 7.28 (SH, s)

(Referential Example 8)

(±)-1-(4-fluorophenyl)-3-[3-(1-phenylmethyl) piperidyl]-2-imidazolidinone

Using (±)-1-phenylmethyl-3-aminopiperidine as a stating material, title compound was synthesized similarly to Referential examples 1 and 2 and Example 1.

The starting material, (±)-1-phenylmethyl-3-aminopiperidine was synthesized from (±)-ethyl nipecotate similarly to Referential examples 6 and 7.

m.p. 118°–119° C. (2-prepanol-n-hexane) colorless prisms Elemental analysis (%); As C$_{21}$H$_{24}$FN$_3$ O Calculated; C: 71.36 H: 6.84 N: 11.89 Found; C: 71.56 H: 6.89 N: 11.89

(Referential Example 9)

(S)-1-(4-fluorophenyl)-3-[3-(1-phenylmethyl) piperidyl]-2-imidazolidinone

Using (S)-1-phenylmethyl-3-aminopiperidine as a starting material, title compound was synthesized similarly to Referential examples 1 and 2 and Example 1.

The starting material, (S)-1-phenylmethyl-3-aminopiperidine was synthesized similarly to referential examples 6 and 7, after (s)-ethyl nipecotate from (±)-ethyl nipecotate was synthesized by the method described in Recueil. Travl. chim. Pays-Bas, 70, 899 (1951).

m.p. 121.5°–122.5° C. (2-propanol) colorless prisms $[\alpha]_D^{26}=-11°$ (1=50, c 4.9, CHCl$_3$) Elemental analysis (%); As C$_{21}$H$_{24}$FN$_3$ O Calculated; C: 71.36 H: 6.84 N: 11.89 Found; C: 71.47 H: 6.88 N: 11.69

(EXAMPLE 3)

(R)-1-(3,4-dimethoxyphenyl)-3-[3-(1-phenylmethyl)piperidyl]-2-imidazolidinone

To a 30 ml anhydrous tetrahydrofuran solution of 3.02 g (8.17 mmoi) of (R)-N-3,4-dimethoxyphenyl-N'-3-(1-phenylmethyl)piperidylethylenediamine in a 200 ml rounmd-bottomed flask were added 2.65 g (2 eg.) of N,N'-carbonyldiimidazole (CDI) at room temperature, and the mixture was refluxed for 2 hours. Thereafter, solvent was distilled off at 100° C. in an oil bath under atmospheric pressure to obtain the residue, which was allowed to stand overnight. The temperature of this residue was returned to room temperature and ice was added by portions, then 200 ml of methylene chloride were added further to extract and separate the organic layer. The aqueous layer was made to be pH of 12 or higher with 2N potassium hydroxide, which was extracted with methylene chloride (100 ml×2). These methylene chloride layers were combined with previously extracted layer, dried over anhydrous sodium sulfate, and then solvent was distilled off under reduced pressure to obtain a brown oil. This was purified by column chromatography (silica gel., ethyl acetate) and then recrystallized to obtain 1.94 g (yield 60 %) of title compound.

m.p. 131°–132° C. (2-propanol) colorless needles $[\alpha]_D^{30}=$+14° (1–50, c. 3.2, chloroform) Elemental analysis (%); As C$_{23}$H$_{29}$N$_3$ O$_3$ Calculated; C: 69.85 H: 7.39 N: 10.62 Found; C: 69.66 H: 7.58 N: 10.56

The starting material, (R)-N-3,4-dimethoxyphenyl-N'-3-(1-phenylmethyl)piperidylethylenediamine was synthesized similarly to Referential example 1 and Referential example 2.

(EXAMPLE 4)

(R)-1-(4-fluorophenyl)-3-[3-[1-(4-chlorophenylmethyl)]-peperidyl]-2-imidazolidinone To a 20 ml dried acetonitrile solution of 0.55 g (2.09 mmol) of (R)-1-(4-fluorophenyl)-3-(3-piperidyl)-2-imidazolidinone in a 50 ml round-bottomed flask were added 0.31 g (1.07 eg.) of potassium carbonate and 0.45 g (1.05 of 4-chlorobenzyl bromide in turn at room temperature under stirring, and the mixture was refluxed for 3 hours. Thereafter, methylene chloride was added to the reaction mixture, the inorganics were collected by filtration, and the filtrate was distilled off under reduced pressure. The residue obtained was dissolved into methylene chloride, washed with saturated solution of sodium hydrogencarbonate, and the extracted organic layer was dried over anhydrous sodium sulfate. Solvent was distilled off and the residue thus obtained was recrystallized to obtain 0.55 g (yield 68 %) of title compound.

m.p. 151°–152° C. (2 - propanol) pale yellow needls $[\alpha]_D^{31}=-2.0°$ (1–50, c. 2.3, chloroform) Elemental analysis (%); As C$_{21}$H$_{23}$ClFN$_3$ O Calculated; C: 65.03 H: 5.98 N: 10.83 Found; C: 64.91 H: 6.05 N: 10.68

(EXAMPLE 5)

(R)-1-(4-fluorophenyl)-3-[3-[1-(2-fluorophenylmethyl)]-piperidyl]-2-imidazolidinone A mixture of 0.50 g (1.90 mmol) of (R)-1-(4-fluorophenyl)-3-(3-piperidyl)-2-imidazolidinone, 0.28 g (1.02 eg.) of o-fluorophenylbenzyl chloride, 0.29 g (1.51 eg.) of triethylamine and 10 ml of ethanol in a 200 ml round-bottomed flask was refluxed for 1.75 hours. Thereafter, the reaction mixture was distilied off under reduced pressure, water was poured to the residue, and it was made alkaline with aqueous ammonia, which was extracted with ethyl acetate. The extracted organic layers were combined and dried over anhydrous sodium sulfate. Solvent was distilled off under reduced pressure and the residue thus obtained was purified by column chromatography (silica gel, ethyl acetate:n-hexane 2:1), then recrystallized to obtain 0.45 g (yield 64 %) of title compound.

m.p. 96°–97° C. (ethyl acetate: n-hexane) white plates $[\alpha]_D^{27}=+20°$ (1=50, e. 2.1 chloroform) Elemental analysis (%); As C$_{21}$H$_{23}$F$_3$ N$_3$ O Calculated; C: 67.91 H: 6.24 N: 11.31 Found; C: 67.88 H: 6.43 N: 11.32

(EXAMPLE 6)

(R)-1-(4-fluorophenyl)-3-[3-[1-(3,4-methylenedioxyphenylmethyl]piperidyl]-2-imidazolidinone To 0.35 g (1.10 eg.) of 3,4-methylenedioxybenzyl alcohol in a 50 ml round-bottomed flask were added 1.68 ml (11 eg.) of thionyl chloride by portions at room temperature, and the mixture was reacted for 3 hours at room temperature as it is. Carbon tetrachloride was added to the reaction mixture and distilled off under reduced pressure. Then, the residue was treated azeotropically again with carbon tetrachloride and toluene. The residue obtained was dissolved into 20 ml of dried acetonitrile at room temperature and, after added 0.55 g (2.09 mmol) of (R)-1-(4-fluorophenyl)-3-(3-piperidyl)-2-imidazolidinone and 0.31 g (1.07 eg.) of potassium carbonate in turn to this, the mixture was refluxed for 2 hours. Thereafter, the reaction mixture was poured into water, which was extracted with ethyl acetate. The extracted organic layers were combined and dried over anhydrous sodium sulfate. Then, solvent was distilled off under reduced pressure and the residue thus obtained was recrystallized to obtain 0.30 g (yield 36 %) of title compound.

m.p. 155°–156° C. (acetonitrile) colorless prisms $[\alpha]_D^{30}=$ −1.5° (1=50 c. 2.6 chloroform) Elemental analysis (%), As C$_{22}$H$_{24}$FN$_3$ O$_3$ Calculated; C: 66.48 H: 6.09 N: 10.57 Found; C: 66.43 H: 6.19 N: 10.73

(EXAMPLE 7)

(R)-1-(4-fluorophenyl)-3-[3-[1-(2-methoxyphenylmethyl)]-piperidyl]-2-imidazolidinone To 0.26 g (0.99 eg.) of 2-methoxybenzyl alcohol in a 200 ml round-bottomed flask were added 2.00 ml (excess amount) of thionyl chloride by portions at room temperature, and, after reacted the mixture for 1 hour at room temperature as it is, the reaction mixture was distilled off under reduced pressure.

To the residue obtained were added 10 ml of ethanol, 0.50 g (1.90 mmol) of (R)-1-(4-fluorophenyl)-3-(3-piperidyl)-2-imidazolidinone and 0.29 g (1.51 eg.) of triethylamine in turn at room temperature, and the mixture was refluxed for 4 hours. Thereafter, the reaction mixture was distilled off under reduced pressure, water was poured to the residue, and it was made alkaline with aqueous ammonia, which was extracted with ethyl acetate. The extracted organic layers were combined and dried over anhydrous sodium sulfate. Solvent was distilled off under reduced pressure and the residue thus obtained was purified by column chromatography (silica gel, ethyl acetate), then distilled under reduced pressure to obtain 0.11 g (yield 35%) of title compound.

b.p. 310° C./0.8 mmHg Yellow oil $[\alpha]_D^{22}=+23°$ (1=50, c. 1.1, chloroform) Elemental analysis (%); As $C_{22}H_{26}FN_3O_2$ Calculated; C: 68.91 H: 6.83 N: 10.96 Found; C: 68.72 H: 6.86 N: 10.98

The starting material, (R)-1-(4-fluorophenyl)-3-(3-piperidyl)-2-imidazolidinone was synthesized as follows:

(Referential Example 10)

(R)-1-(4-fluorohenyl)-3-(3-piperidyl)-2-imidazolidinone

To a 150 ml methanol solution of 5.50 g (15.6 mmol) of (R)-1-(4-fluorophenyl)-3-[3-(1-phenylmethyl)piperidyl]-2-imidazolidinone (Example 1) in a 300 ml round-bottomed flask were added 1.96 g (2 eg.) of ammonium formate and a 30 ml aqueous suspension of 0.83 g (15 % amounts) of 10 % Pd-C were added in turn at room temperature, and this reaction mixture was refluxed for 4 hours. The temperature of reaction mixture was cooled to room temperature, catalyst was collected by filtration, and the filtrate was distilled off under reduced pressure. The residue thus obtained was recrystallized to obtain 2.23 g (yield 54 %) of title compound.

m.p. 167°–168° C. (acetonitrile) colorless prisms $[E]_D^{24}=+13°$ (1=50, c. 5.5, chloroform) Elemental analysis; As $C_{14}H_{18}FN_3O\ 0.2H_2O$ Calculated; C: 63.00 H: 6.95 N: 15.74 Found; C: 62.92 H: 6.85 N: 15.86

(EXAMPLES 8 THROUGH 27)

Following compounds were synthesized by the similar methods to Examples 4 through 7, using (R)-1-(r-fluorophenyl)-3-(3-piperidyl)-2-imidazolidinone (Referential example 10) as a starting material.

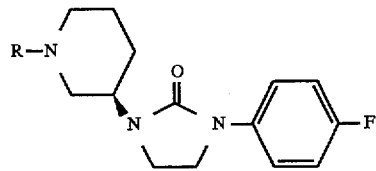

TABLE 1

| Example | R | Melting point (Solvent for recrystallization) | Specific rotation** (c. concentration, solvent) | Elemental analysis (%) calculated/Found |
|---|---|---|---|---|
| 8 | (3-F-benzyl) | 96–97° C. (n-Hexane: AcOEt) | $[\alpha]_D^{27}=$ +6.3° (c.2.2, CHCl₃) | $C_{21}H_{21}F_2N_3O$ C: 67.91 H: 6.24 N: 11.31 C: 67.86 H: 6.29 N: 11.30 |
| 9 | (4-F-benzyl) | 105–106° C. (n-Hexane: AcOEt) | $[\alpha]_D^{27}=$ +7.0° (c.2.3, CHCl₃) | $C_{21}H_{21}F_2N_3O$ C: 67.91 H: 6.24 N: 11.31 C: 68.19 H: 6.14 N: 11.23 |
| 10 | (2-Me-benzyl) | 115–117° C. (n-Hexane: AcOEt) | $[\alpha]_D^{27}=$ +8.0° (c.2.6, CHCl₃) | $C_{22}H_{26}FN_3O$ C: 71.91 H: 7.13 N: 11.44 C: 71.87 H: 7.38 N: 11.30 |
| 11 | (3-Me-benzyl) | 95° C. (n-Hexane: AcOEt) | $[\alpha]_D^{27}=$ +8.5° (c.2.0, CHCl₃) | $C_{22}H_{26}FN_3O$ C: 71.91 H: 7.13 N: 11.44 C: 72.02 H: 7.26 N: 11.39 |
| 12 | (4-Me-benzyl) | 162–163° C. (n-Hexane: AcOEt) | $[\alpha]_D^{27}=$ +7.9° (c.2.2, CHCl₃) | $C_{22}H_{26}FN_3O$ C: 71.91 H: 7.13 N: 11.44 C: 72.06 H: 7.25 N: 11.40 |
| 13 | (4-O₂N-benzyl) | 119–121° C. (n-Hexane: AcOEt) | $[\alpha]_D^{27}=$ −23° (c.2.6, CHCl₃) | $C_{21}H_{23}FN_4O_3$ C: 63.31 H: 5.82 N: 14.06 C: 63.30 H: 5.90 N: 14.07 |

TABLE 1-continued

| Example | R | Melting point (Solvent for recrystallization) | Specific rotation** (c. concentration, solvent) | Elemental analysis (%) calculated/Found |
|---|---|---|---|---|
| 14 | MeO-C6H4-CH2CH< | 141–142° C. (n-Hexane: AcOEt) | $[\alpha]_D^{27}=$ +4.3° (c.2.1, CHCl$_3$) | C$_{22}$H$_{26}$FN$_3$O$_2$ C: 68.91 H: 6.83 N: 10.96 C: 68.77 H: 6.97 N: 10.88 |
| 15 | F$_3$C-C6H4-CH2CH< | 168° C. (n-Hexane: AcOEt) | $[\alpha]_D^{27}=$ +4.7° (c.2.1, CHCl$_3$) | C$_{22}$H$_{23}$F$_4$N$_3$O C: 62.70 H: 5.50 N: 9.97 C: 63.06 H: 5.48 N: 9.98 |

**1 = 50

TABLE 2

| Example | R | Melting point (Solvent for recrystallization) | Specific rotation** (c. concentration, solvent) | Elemental analysis (%) calculated/Found |
|---|---|---|---|---|
| 16 | C6H5-CH2CH< | 137–138° C. (iso-Pr$_2$O) | $[\alpha]_D^{28}=$ +3.7° (c.2.9, CHCl$_3$) | C$_{23}$H$_{26}$FN$_3$O C: 71.91 H: 7.13 N: 11.44 C: 71.73 H: 7.26 N: 11.41 |
| 17 | Br-C6H4-CH2CH< | 180–181° C. (CH$_3$CN) | $[\alpha]_D^{31}=$ −5.4° (c.2.8, CHCl$_3$) | C$_{21}$H$_{27}$BrFN$_3$O C: 58.34 H: 5.36 N: 9.72 C: 58.17 H: 5.42 N: 9.73 |
| 18 | NC-C6H4-CH2CH< | 115–116° C. (2-PrOH: iso-Pr$_2$O) | $[\alpha]_D^{30}=$ −20° (c.2.5, CHCl$_3$) | C$_{22}$H$_{23}$FN$_4$O C: 69.82 H: 6.13 N: 14.80 C: 70.02 H: 6.14 N: 14.77 |
| 19 | tBu-C6H4-CH2CH< | 113–114° C. (n-Hexane) | $[\alpha]_D^{30}=$ +2.4° (c.2.3, CHCl$_3$) | C$_{25}$H$_{32}$FN$_3$O C: 73.32 H: 7.88 N: 10.26 C: 73.35 H: 7.91 N: 10.13 |
| 20 | C6H5-C6H4-CH2CH< | 136–137° C. (CH$_3$CN) | $[\alpha]_D^{30}=$ −13° (c.1.6, CHCl$_3$) | C$_{22}$H$_{28}$FN$_3$O C: 75.50 H: 6.57 N: 9.78 C: 75.61 H: 6.72 N: 9.79 |
| 21 | EtO-C6H4-CH2CH< | 138–139° C. (CH$_3$CN-2-PrOH) | $[\alpha]_D^{28}=$ +4.5° (c.2.3, CHCl$_3$) | C$_{23}$H$_{28}$FN$_3$O$_2$ C: 69.50 H: 7.10 N: 10.57 C: 69.41 H: 7.25 N: 10.45 |
| 22 | iPr-C6H4-CH2CH< | 103–104° C. (n-Hexane) | $[\alpha]_D^{31}=$ +3.5° (c.2.4, CHCl$_3$) | C$_{24}$H$_{30}$FN$_3$O C: 72.88 H: 7.65 N: 10.62 C: 72.94 H: 7.73 N: 10.59 |
| 23 | MeS-C6H4-CH2CH< | 141–142° C. (2-PrOH) | $[\alpha]_D^{29}=$ −5.6° (c.2.6, CHCl$_3$) | C$_{22}$H$_{26}$FN$_3$OS C: 66.14 H: 6.56 N: 10.52 C: 66.14 H: 6.83 N: 10.50 |

**1 = 50

TABLE 3

| Example | R | Melting point (Solvent for recrystal-lization) | Specific rotation** (c. concentration, solvent) | Elemental analysis (%) calculated/Found |
|---|---|---|---|---|
| 24 | Et—⟨phenyl⟩—CH₂ (4-ethylbenzyl) | 136–137° C. (2-PrOH) | $[\alpha]_D^{29}=$ +5.8° (c.1.8, CHCl₃) | $C_{23}H_{28}FN_3O$<br>C: 72.41 H: 7.40 N: 11.01<br>C: 72.36 H: 7.64 N: 11.00 |
| 25 | Me—⟨phenyl(Me)⟩—CH₂ (3,4-dimethylbenzyl) | 150–151° C. (2-PrOH) | $[\alpha]_D^{28}=$ +5.4° (c.2.2, CHCl₃) | $C_{23}H_{28}FN_3O$<br>C: 72.41 H: 7.40 N: 11.01<br>C: 72.33 H: 7.31 N: 10.96 |
| 26 | Me, Me—⟨phenyl⟩—CH₂ (3,5-dimethylbenzyl) | 106–107° C. (n-Hexane) | $[\alpha]_D^{31}=$ +6.6° (c.2.5, CHCl₃) | $C_{23}H_{28}FN_3O$<br>C: 72.41 H: 7.40 N: 11.01<br>C: 72.32 H: 7.43 N: 10.95 |
| 27 | tBu—⟨phenyl⟩—CH₂ (4-tert-butylbenzyl) | 247–249° C. (CH₃CN) | $[\alpha]_D^{30}=$ +51° (c.1.9, CHCl₃) | $C_{25}H_{32}FN_3$ O HCl 0.2H₂O<br>C: 66.79 H: 7.49 N: 9.35<br>C: 66.94 H: 7.66 N: 9.35 |

*HCl salt
**1 = 50

(EXAMPLE 28)

(R)-1-(2-fluorophenyl)-3-[3-(1-phenylmethyl) piperidyl]-2-imidazolidinone

To 0.76 g (1.9.7 mmol) of (R)-N-3-(1-phenylmethyl)-piperidyl-N'-(2-methoxyethyl)-N'-2-fluorophenylurea were added dropwise 20 ml of 48 % hydrobromic acid under stirring and cooling with ice, and then the mixture was refluxed for 8 hours. The reaction mixture was poured into ice water and potassium hydroxide was added to this under cooling with ice to make pH 12 or higher, which was extracted thrice with 20 ml of methylene chloride. The extracted solutions were combined and dried over anhydrous sodium sulfate. Then, solvent was distilled off under reduced pressure and the residue thus obtained was purified by column chromatography (alumina, ethyl acetate:nhexane= 1:1). It was then crystallized at 5° C. and recrystallized to obtain 0.37 g (yield 53 %) of title compound.

m.p. 90°–92° C. (n–hexane) colorless powders $[\alpha]_D^{25}$=+ 9.8° (1=50, c. 1.0, hloroform) Elemental analysis (%); As $C_{21}H_{24}FN_3$ O Calculated; C: 71.36 H: 6.84 N: 11.89 Found; C: 71.21 H: 6.84 N: 12.03

The starting material, (R)-N-3-(1-phenylmethyl) piperidyl-N-(2-methoxyethyl)-N'-2-fluorophenylurea was synthesized as follows:

(Referential Example 11)

(R)-3-(methoxyacetylamino)-1-phenylmethylpiperidine

To a 50 ml anhydrous tetrahydrofuran solution of 5.00 g (26.3 mmol) of (R)-1-phenylmethyl-3-aminopiperidine (Referential example 7) in a 300 ml three-necked flask was added a 50 ml anhydrous tetrahydrofuran solution of 3.20 g (1.2 eg.) of triethylamine, and, to this reaction mixture was added dropwise a 50 ml anhydrous tetrahydrofuran solution of 2.85 g (1.0 eg.) of methoxyacetyl chloride under stirring and cooling with ice. After reacted for 5 hours at room temperature, methylene chloride and small amount of water were added to extract (20 ml×6). The organic layers were combined and dried over anhydrous sodium sulfate. Then, solvent was distilled off under reduced pressure and the residue thus obtained was purified by column chromatography (alumina, ethyl acetate:n-hexane=1:1) to obtain 6.67 g (yield 97 %) of title compound as a pale yellow oil.

$[\alpha]_D^{20}$=+6.4° (1=50, c. 2.0, ethanol) MASS; As $C_{15}H_{22}N_2O_2$ m/e; 262 (M⁺, base) 217, 173

(Referential Example 12)

(R)-3-(2-methoxyethylamino)-1-phenylmethylpiperidine

To a 50 ml anhydrous tetrahydrofuran suspension of 0.87 g (2.0 eg.) of lithium aluminum hydride in a 300 ml round-bottomed flask was added dropwise a 20 ml anhydrous tetrahydrofuran solution of 3.00 g (11.4 mmol) of (R)-3-(2-methoxyacetylamino)-1-phenylmethylpiperidine. After stirred for 1 hour at room temperature, the reaction mixture was refluxed for 3 hours. Further, 0.87 g (2.0 eg.) of lithium aluminum hydride were added and the mixture was refluxed for 3 hours. The reaction mixture was stirred under cooling with ice and, after added 180 ml of ethyl acetate and a 10 ml aqueous solution of sodium hydroxide (1.82 g, 4.0 eg.) in turn to this and stirred for 30 minutes, anhydrous magnesium sulfate was added and it was filtered with celite. The filtrate was distilled off under reduced pressure and the residue thus obtained was purified by column chromatography (alumina, ethyl acetate:n-hexane=1:2) to obtain 2.03 g (yield 72 %) of title compound as a brown oil.

$[\alpha]_D^{25}=-10°$ (1=50, c. 1.0, ethyl acetate) MASS; As $C_{15}H_{24}N_2$ O m/e; 248 (M$^+$), 216, 173, 147 (base), 134

(Referential Example 13)

(R)-N-3-(1-phenylmethyl)piperidyl-N-(2-methoxyethyl)-N'-2-fluorophenylurea

To a 20 ml dried methylene chloride solution of 1.00 g (4.03 mmol) of (R)-3-(2-methoxyethylamino)-1-phenylmethylpiperidine in a 100 ml round-bottomed flask was added dropwise a solution of 0.55 g (1.0 eg.) of 2-fluorophenylisocyanate in methylene chloride 5 ml under stirring and cooling with ice. After stirred the reaction mixture for 8 hours at room temperature, solvent was distilled off under reduced pressure and the residue obtained was dissolved into 30 ml of methylene chloride, which was extracted with 20 ml of 3N hydrochloric acid (×4). This hydrochloric acid layer was made to be pH of 12 or higher with diluted aqueous solution of potassium hydroxide under cooling with ice. This was extracted with 20 ml of methylene chloride (×4), then dried over anhydrous sodium sulfate, and solvent was distilled off under reduced pressure. The residue thus obtained was purified by column chromatography (ethyl acetate:n-hexane=1:2) to obtain 0.85 g (yield 55 %) of title compound as a pale yellow oil.

$[\alpha]_D^{23}=+15°$ (1=50, c. 1.2, ethyl acetate) MASS; As $C_{22}H_{28}FN_3$ $O_2$ m/e; 385 (M$^+$), 354, 248, 174 (base), 134

(EXAMPLE 29)

(R)-1-(3-fluorophenyl)-3-[3-(1-phenylmethyl)piperidyl]-2-imidazolidinone

Using (R)-N-3-(1-phenylmethyl)piperidyl-N-(2-methoxyethyl)-N'-3-fluorophenylurea, title compound was synthesized similarly to Example 28.

m.p. 84°–86° C. (n–hexane) colorless needles $[\alpha]_D^{26}=11°$ (1=50, c. 1.0, chloroform) Elemental analysis (%); As $C_{21}H_{24}FN_3$ O Calculated; C: 71.36 H: 6.84 N: 11.89 Found; C: 71.25 H: 6.96 N: 11.67

The starting material, (R)-N-3-(1-phenylmethyl)piperidyl-N-(2-methoxyethyl)-N'-3-fluorophenylurea was synthesized similarly to Referential example 13, using (R)-3-(2-methoxyethylamino)-1-phenylmethylpiperidine (Referential example 12) and 3-fluorophenylisocyanic acid.

(Referential Example 14)

(R)-N-3-(1-phenylmethyl)piperidyl-N-(2-methoxyethyl)-N'-3-fluorophenylurea m.p. 91°–94° C. (n–hexane) colorless powders $[\alpha]_D^{22}=+17°$ (1=50, c. 1.0, ethyl acetate) MASS; As $C_{22}H_{28}FN_3$ $O_2$ m/e; 385 (M$^+$), 354, 173, 147, 91 (base)

(Experimental Example 1)

In Vitro Biochemical Test
1) Radioligand binding experiment to $M_1$ type muscarinic cholinergic receptor Method: To a crude synaptic membrane specimen prepared from all brains (except cerebellum and brain stem) of rat, [$^3$H]-pirenzepine ([$^3$H]-PZ, final oncentration: 1 nM) and testing compound were added and the mixture was incubated for 60 minutes at 25 ° C. After stopped the reaction by high-speed suction filtration, the radioactivity on filter was measured with liquid scintillation counter. The specific binding level of [$^3$H]-pirenzepine was determined by subtracting the nonspecific binding level in the presence of atropine (1 µM) from total binding level. Putting the [$^3$H]-pirenzepine binding in the absence of testing compound on 100, the concentration of compound to decrease by 50 % (IC$_{50}$ value) was made an index of the binding activity of compound to $M_1$ muscarinic receptor (refer to: J. A. D. M. Toner et al, Life Science, 1987, 40, 1981–1987).

2) Radiolignd binding experiment to $M_2$ type muscarinic cholinergic recetor

Method: Similar procedures were conducted to the experiment on the affinity to $M_1$ receptor, except that the crude synaptic membrane specimen was prepared from the brain stem (medulla oblongata-pons) of rat and [$^3$H]-quinuclidyl benzoate ([$^3$H]-QNB, 0.1 nM) was used as a radioactive ligand.

3) Selectivity to $M_1$ receptor

This was determined from the ratio of IC$_{50}$ values of compound obtained from the binding experiments of $M_1$ and $M_2$ muscarinic receptors.

$$\text{Receptor selectivity} = \frac{IC_{50} \text{ value } ([^3H] - QNB)}{IC_{50} \text{ value } ([^3H] - PZ)}$$

TABLE 4

| No. of compound | [$^3$H]-PZ ($M_1$) IC$_{50}$ µM | [$^3$H]-QNB ($M_2$) IC$_{50}$ µM | IC$_{50}$ ($M_2$)/IC$_{50}$ ($M_1$) |
| --- | --- | --- | --- |
| Example 1 | 0.03 | 0.5 | 16.7 |
| Referential example 8 | 0.08 | 1.09 | 13.6 |
| Referential example 9 | 3.7 | >10.0 | >2.7 |

Results: Table 4 shows the affinity and selectivity of the inventive compound to $M_1$ and $M_2$ receptors. IC$_{50}$ value of [$^3$H]-PZ denotes the affinity to $M_1$ receptor and IC$_{50}$ value of [$^3$H]-QNB the affinity to $M_2$ receptor. It is shown that the higher the ratio of $M_2/M_1$, the higher the selectivity to $M_1$ receptor.

The reusults show that the inventive compound has patent affinity to the central $M_1$ muscarinic receptor and that it has far higher selectivity to $M_1$ receptor than to $M_2$ receptor. Besides, in the affinity to receptors, the compound of the invention (R isomer) is about 3 times more excellent than that of Referential example 8 (racemic form) and about 120 times more excellent than that of Referential example 9 (S isomer).

(Experimental Example 2)

In vivo pharmacological test
Testing on the pirenzepine-induced amnesia

For the experiment animals, Std:ddY strain male mice with body weight of 24 to 34 g (age in week: 5–6) (Nippon SLC) were used. For the device, a step-through type passive avoidance apparatus (made by Ohara Medical Co., Ltd.) consisting of two tight and dark rooms was used. In the acquisition trial, mouse was placed in the light room and, 10 seconds later, the partitive guillotine door was opened. As soon as the mouse moved into the dark room, the guillotine door was closed and electric shock of 41 to 45 V was given for 1 second through the metal grid bars of the floor. The retention trial was conducted 24 hours later since then. In the retention trial, mouse was placed again in the light room and the time until they moved into the dark room was measured for at maximum 300 seconds as a reaction latency; for mouse exhibited longer latency than those, the time was made to be 300 seconds. The induction of amnesia was performed by fixing a mouse at prone position without anesthetization at 20 minutes before learning acquisition trial and injecting pirenzepine (10 μg/2 μl/mouse bilaterally into cerebral ventricles using a microsyringe. Moreover, a group not to administered with pirenzepine before acquisition trial (non-amnesia comparison group) was also provided. The mice were made to be 12 to 21 animals per group and the testing compound was administered orally at 30 or 60 minutes before acquisition trial. The improvement rate was calculate according to following equation and the results are shown in Table 5 (refer to: M. P. Callfield et at, J. Pharm. Pharmacol. 1983, 35, 131–132).

TABLE 6

| No. of compound | Dose (mg/kg) | | |
|---|---|---|---|
| | 300 | 600 | 1200 |
| Example 1 | None | None | None |
| Referential example 8 | None | Convulsion 3/4 | Death 4/4 |
| Referential example 9 | Convulsion 2/4 Death 1/4 | Death 4/4 | — |

Improvement rate = (Latency of compound-administered amnesia group − latency of pirenzepine-treated group) / (Latency of non-amnesia comparison group − latency of pirenzepine-treated group) × 100

TABLE 5

| Compound | Dose (mg/kg) | Number of animals used | Reaction latency Mean ± S.E. | Improvement rate (%) |
|---|---|---|---|---|
| Non-treated | — | 13 | 154.0 ± 29.7## | |
| Pirenzepine - treated mouse | — | 13 | 58.8 ± 27.1 | |
| Example 1 | 3 | 13 | 91.5 ± 21.4 | 34.3 |
| | 10 | 13 | 133.0 ± 29.3# | 77.9 |
| | 30 | 12 | 166.9 ± 40.2# | 113.6 |
| Non-treated | — | 21 | 276.0 ± 12.9## | |
| Pirenzepine - treated mouse | — | 21 | 93.0 ± 26.1 | |
| Referential example 8 | 3 | 21 | 55.1 ± 20.0 | −20.7 |
| | 10 | 21 | 153.7 ± 27.6# | 33.2 |
| Non-treated | — | 12 | 211.6 ± 26.2# | |
| Pirenzepine - treated mouse | — | 12 | 91.5 ± 30.3 | |
| Referential example 9 | 3 | 12 | 63.3 ± 32.1 | −23.5 |
| | 10 | 12 | 61.5 ± 26.5 | −25.0 |
| | 30 | 13 | 113.2 ± 36.2 | 18.1 |

*: $p < 0.05$  ##: $p < 0.01$ With significant difference against pyrenezepine-treated mice Results: Table 5 shows the improvement effect of the inventive compound on the pirenzepine-induced amnesia.

The reduction of the reaction latency of pirenzepine-treated mice relative to the group without treatment indicates that the decreased learning effect due to electric shock, that is, amnesia is caused. The extension of the reaction latency with compound therefore means the improved amnesia.

The results show that the inventive compound (R isomer) and the compound of Referential example 8 (racemic form) have very excellent improvement effect on the amnesia caused by the disturbance of central cholinergic nerves. On the contrary, the compound of Referential example 9 (S isomer) could not improve the amnesia induced with pyrenezepine.

(Experimental Example 3)

In Vivo Toxicity Test

For the experiment animals, 4 animals per group of Std:ddY strain male mice with body weightOf 26 to 30 g (age in week: 5) (Nippon SLC) were used. The testing compound was suspended into 5 % solution of arabic gum and administered orally. The common symptoms and death caused with compound were recorded for 3 days after administration.

Results: Table 6 shows the common symptoms and death appearing at the time of administering the inventive compound.

With the compound of Referential example 8 (racemic form), the convulsion was observed at 600 mg/kg and the death of 1200 mg/kg, and, with the compound of Referential example 9 (S isomer), both convulsion and death were observed at the administration of 300 mg/kg or more. Whereas, with the compound of the invention, such symptom was not caused even at 1200 mg/kg. It was suggested that the toxic action exhibited with racemic form depended on the S isomer.

Utilizability in the Industry

As described above, the optically active imidazolidinone derivatives or their acid adducts with functionally cholinergic activity (muscarine $M_1$ activity) are useful as therapeutic drugs of senile dementia.

We claim:

1. A stereoisomer 3-(R)-imidazolidinonyl piperidine of the following structure:

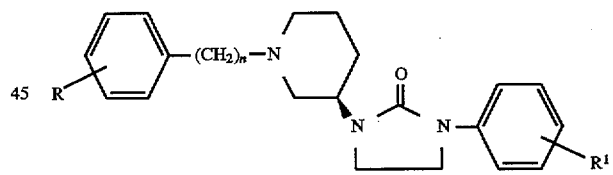

(wherein R and $R^1$ denote identically or differently hydrogen atoms, halogen atoms, lower alkyl groups which may be substituted by halogen atoms, lower alkoxy groups, lower alkylthio groups, lower alkoxycarbonyl groups, nitro groups, amino groups or cyano groups, and n denotes 1 to 4), or an acid addition salt.

2. The stereoisomer of claim 1, wherein R is a hydrogen atom, $R^1$ is any of halogen atom, lower alkyl group which may be substituted by halogen atom and lower alkoxy group, and n is 1, or an acid addition salt.

3. The stereoisomer of claim 1, wherein $R^1$ is a halogen atom, R is any of halogen atom, lower alkyl group which may be substituted by halogen atom and lower alkoxy group, and n is 1, or an acid addition salt.

4. The stereoisomer of claim 1, wherein the stereoisorner is (R)-1-(3-fluorophenyl)-3-[3-(1-phenylmethylpiperidyl)]-2-imidazolidinone.

5. The stereoisomer of claim 1, wherein the stereoisomer is (R)-1-(4-trifluoromethylphenyl)-3-[3-(1-phenylmethylpiperidyl)]-2-imidazolidinone.

6. The stereoisomer of claim 1, wherein the stereoisomer is (R)-1-(3-trifluoromethylphenyl)-3-[3-(1-phenylmethylpiperidyl)]-2-imidazolidinone.

7. The stereoisomer of claim 1 having the following formula:

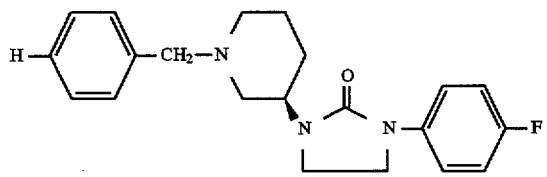

8. The stereoisomer of claim 1 having the following formula:

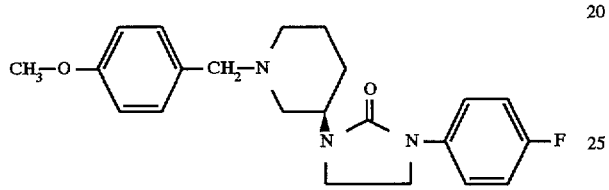

9. The composition of claim 8, wherein the stereoisomer has the following formula:

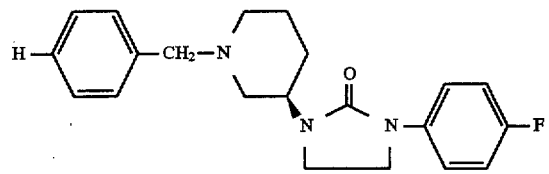

10. The composition of claim 8, wherein the stereoisomer has the following formula:

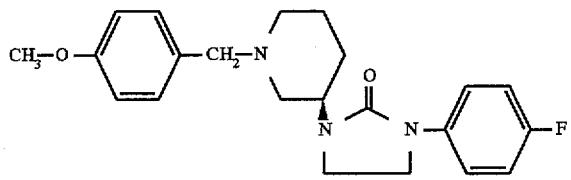

11. A pharmaceutical composition comprising a therapeutically effective amount of a stereoisomer 3-(R)-imidazolidinonyl piperidine of the following structure:

(wherein R and $R^1$ denote identically or differently hydrogen atoms, halogen atoms, lower alkyl groups which may be substituted by halogen atoms, lower alkoxy groups, lower alkylthio groups, lower alkoxycarbonyl groups, nitro groups, amino groups or cyano groups, and n denotes 1 to 4), or an acid addition salt, and a pharmaceutically acceptable carrier.

* * * * *